United States Patent [19]

Toma et al.

[11] Patent Number: 5,021,340
[45] Date of Patent: Jun. 4, 1991

[54] **CLONING VECTOR, MOLECULES OF RECOMBINANT DNA, *BACILLUS SUBTILIS* STRAINS TRANSFORMED WITH THE SAID MOLECULES AND METHODS FOR THE EXPRESSION OF HETEROLOGOUS GENES AND THE PRODUCTION AND SECRETION OF PROTEINS CODED BY THE SAID GENES**

[75] Inventors: Salvatore Toma; Marina Del Bue, both of Milan; Antonio Mele, Pavia; Guido Grandi, Segrate, all of Italy

[73] Assignee: Eniricerche S.p.A., Milan, Italy

[21] Appl. No.: 395,173

[22] Filed: Aug. 17, 1989

Related U.S. Application Data

[63] Continuation of Ser. No. 884,238, Jul. 10, 1986, abandoned.

[30] Foreign Application Priority Data

Jul. 10, 1985 [IT] Italy .............................. 21507 A/85

[51] Int. Cl.$^5$ .................... C12N 1/21; C12N 15/09; C12N 15/75
[52] U.S. Cl. ............................... 435/69.1; 435/71.1; 435/91; 435/170; 435/172.1; 435/172.3; 435/252.31; 435/320.1; 435/839; 536/27; 935/6; 935/8; 935/9; 935/22; 935/29; 935/33; 935/38; 935/59; 935/60; 935/61; 935/74
[58] Field of Search ............... 435/68, 91, 176, 172.1, 435/172, 3, 253, 320, 839, 69.1, 71.1, 91, 170, 252.31, 536; 536/27; 935/6, 8, 9, 10, 13, 22, 23, 29, 33, 44, 47, 48, 60, 61, 74, 38, 59

[56] References Cited

FOREIGN PATENT DOCUMENTS

0133756 3/1985 European Pat. Off. .

OTHER PUBLICATIONS

Ohmura et al. 1984, *J. Biochem* 95:87.
Yang et al. 1984, *J. Bacteriol* 160:15.
Uehara et al. 1979, *J. Bacteriol* 139:583.
Craig et al. 1982 *Nature* 295:345.
Yamazaki et al. 1983 *J. Bacteriol* 156: 327.

*Primary Examiner*—Richard A. Schwartz
*Assistant Examiner*—Richard C. Peet
*Attorney, Agent, or Firm*—Sughrue, Mion, Zinn, Macpeak & Seas

[57] ABSTRACT

A description is given of a cloning vector useful for the expression and secretion of heterologous proteins in *Bacillus subtilis*, molecules of recombinant DNA formed by the said cloning vector, expediently cut at a restriction site located within the neutral protease gene, and by the sequence of heterologous DNA which codes for the protein of interest, *Bacillus subtilis* cells transformed with the said molecules and capable of expressing the sequence of heterologous DNA and of producing and secreting the protein coded by the said sequence of heterologous DNA in high yields.

The proteins obtained in this manner are useful in the fields of pharmaceuticals and foods, or as compounds for the production of substances which are normally obtained by chemical synthesis.

11 Claims, 8 Drawing Sheets

FIG. 1

GATCACGCGGGCATCAACACATATAGTGAAAAGCCGCCAGCAGCACATATCCGTATAACAAAAAATGCAGCAGGGCAACAGTTCTTTTCCGTCCTCTCTTAA

GTAAGCGCTGGTGTGAAGTTTGTTGATTGCACCTGGTGAATAAGTTCAACAGACACTCCCGGCTGAATCCGCAACATAACACCCGCCAAGAACATT
                                                                        *

GTGCGGCTGCCGCGGTTTATTTTGGGATGATGCACCAAAAGATATAAGCCCGCCAGAACAACAATTGACCATTGAATCAGCAGGTGCTTTGTCTGCTTAATA

TAAAATAACGTTCGAAATGCAATACATAATGACTGAATAACTCCAACACGAACAACAATCCTTTACTTCTTATTAAGGCCTCATTCGGTTAGACAGCGGGA
                                                        ▼
                                                                                   fMET -----
CTTTTCAAAAAGTTCAAGATGAAACAAAATATCTCATCTTCCCCTTGATAAAAATAAACACAGGACAATACTATCAATTTTGTCTAGTTATGTTAGTT
       P1                                     ===→*  ===→                        ====↑           ←====
TTTGTTAAGTATTCCAGAATGCTGGTTAATATAACAATATAAAGTTTCAGTATTTCAAAAAGGGGGATTTATTGTGGGTTAGGTAAGAAATTGTCT
=== *    P2 *                                                                                 ←---

GTTGCCTGTCGCTGCCTTCGTTATGAGTTTATCAATCAGCCTGAAGGTCATCAGCTTAAAGAGAATCAAACAAATTCCTC

TCCAAAAATGCGATTGCGCAATCAGAACTCTCTGCACCAAATGACAAGGCTGTCAAGCAGTTTTTGAAAAAGAACAGCAACATTTTTAAAGGTGACCCTT
       *                                                                                          *

CCAAAAGGCTG

FIG. 2A

```
GATCACGCGGGCATCAGCATATAGTGAAAAGCCGTCAGCAGGGGCAGCAGTTCTTTTCCGTCCTCTCTTAA
                                        *

GTAAGGCTGGTGAAGTTTGTGATTGCACCTGGTGAATAAGTTCAACAGAGACACTCCGCCAATATAACAACCGCCAAGAACATT
                                                                                *

GTGCGCTGCCGGTTTATTTTGGGATGATGCACCAAAAGATATAAGCCCGCCAGAACAACAATTGACCATTGAATCAGCAGGGTGCTTTGTCTGCTTAATA

TAAATAAACGTTCGAAATGCAATACATAATGACTGAATAACTCCAACACGAACAACAACATCCTTTACTTCTTATTAAGGCCTCATTCGGTTAGACAGCGGA

CTTTTCAAAAAGTTCAAGATGAACAAACAAAATATCTCATCTTCCCCTTGATATGTAAAAAACATAACTCTTGAATGAACCACACATGACACTTGACTCA
                                                *********************************************
                                                                              P1
TCTTGATATATTATTCAACAAAAACAACACACAGGACAATACTATCAATTTTGTCTAGTTATGTTAGTTTTTGTTGAGTATTCCAGAATGCTAGTTAATATA
*************                                   *                                P2    *
   +1    ============== ====→      fMET  ←=:::                ←===
          ACAATATAAAGTTTCAGTATTTCAAAAAGGGGATTTATTGTGGGTTAGGTAAGAAATTGTCTGTTGCTGCTTCGTTATGAGTTTATCAA

TCAGCCTGCCAGGTGTTCAGGCTGCTGAAGGTCATCATCAGCTTAAAGAGAATCAAACAAATTCCTCTCCAAAAACGCGATTGCCAATCAGAACTCTCTGC
                                                                                           *

ACCAAAATGACAAGGCTGTCAAGCAGTTTTTGAAAAAGAACAGCAACATTTTAAAGGTGACCCTTCCAAAAGGCTG
```

CLONING VECTOR, MOLECULES OF RECOMBINANT DNA, *BACILLUS SUBTILIS* STRAINS TRANSFORMED WITH THE SAID MOLECULES AND METHODS FOR THE EXPRESSION OF HETEROLOGOUS GENES AND THE PRODUCTION AND SECRETION OF PROTEINS CODED BY THE SAID GENES

This is a continuation of application Ser. No. 884,238 filed on July 10, 1986, now abandoned.

The present invention relates to the field of molecular biology and, in particular, to a cloning vector in *Bacillus subtilis*, molecules of recombinant DNA, *Bacillus subtilis* strains transformed with the said molecules and methods for the expression of sequences of heterologous DNA and for the production and secretion of proteins coded by the said sequences of heterologous DNA.

More specifically, the present invention relates to the use of a cloning vector for the expression of sequences of heterologous DNA and the production and secretion of the proteins coded by the said sequences in *Bacillus subtilis*, molecules of recombinant DNA which are formed by the cloning vector, expediently cut at a restriction site present within the neutral protease gene, and by the sequence of heterologous DNA which codes for the protein of interest, *Bacillus subtilis* strains transformed with the said molecules of recombinant DNA and capable of expressing the sequence of heterologous DNA and producing and secreting the protein coded by the said sequence, and methods for the expression, production and secretion of the heterologous proteins of interest.

The cloning vector, the molecules of recombinant DNA, the *Bacillus subtilis* strains transformed with the said molecules and the methods of the present invention permit the expression of sequences of heterologous DNA and the production and secretion of proteins coded by the said sequences in high yields. The proteins obtained in this manner are useful in the fields of pharmaceuticals and foods or for the preparation of products which are normally obtained by chemical synthesis.

The capacity of Gram-negative bacteria, such as, for example, *Escherichia coli* (*E. coli*), to express heterologous genes is known.

However, the use of *E. coli* as host for the production of heterologous proteins presents numerous disadvantages. *E. coli* is a pathogenic, Gram-negative bacterium which normally lives in the human or animal intestinal tract, and, moreover, some of the said strains produce endotoxins.

The fermentation processes for the production of heterologous proteins, in which transformed *E. coli* cells are used, must be carried out in closed systems in order to avoid contaminations and infections. All this involves an increase in the production costs.

Moreover, the products synthesized by *E. coli* are retained within the cell.

Accordingly, at the end of the fermentation process, it is necessary to rupture or lyse the cells in order to recover the synthesized products.

Such a treatment involves not only the extraction of the desired product but also the extraction of undesired substances. Accordingly, it is necessary to carry out subsequent processes of separation and purification in order to obtain the product of interest in a form which can be used for man or animals.

All these disadvantages exhibited by *E. coli* make *Bacillus subtilis* a host which is particularly suitable for the production of heterologous proteins.

In fact, *Bacillus subtilis* is a non-pathogenic, Gram-positive bacterium and does not produce endotoxins.

Moreover, in view of the fact that its cells do not have a periplasmic space, the synthesized products may be secreted directly into the culture medium, from which they may be recovered with minor problems of contamination and of purification.

Nevertheless, notwithstanding the numerous advantages exhibited by *Bacillus subtilis*, its use as host for the production of heterologous proteins takes place only rarely, both because of a low level of efficiency in the expression of heterologous genes and because of the low yields with which the proteins coded by the said genes are obtained.

In fact, although genes derived from other species of Bacillus are expressed in *Bacillus subtilis* (Sloma A. et al.: Molecular cloning and nucleotide sequence of the type I $\beta$-lactamase gene from B.cereus. Nucl. Acids Res. II (1983) 4997–5004) and (Gray, O. et al.: Molecular cloning and expression of B. licheniformis $\beta$-lactamase gene in *E. coli* and *Bacillus subtilis*. J.Bacteriol, 145 (1981) 422–428), only few examples of cloning and expression of heterologous genes are reported in the technical literature (Hardy K. et al.: Production in *Bacillus subtilis* of Hepatitis B Core antigene and of major antigene of foot and mouth disease virus. Nature 293 (1981) 481–483).

One of the reasons for such limited use is to be found, above all, in the lack of cloning vectors which permit efficient expression of heterologous genes and high productivity of proteins coded by the said heterologous genes.

In Italian Patent Application 23190-A/84 we have described the hybrid plasmid pSM127, which is capable of stimulating, when introduced into cells of *Bacillus subtilis* SMS108 NRLLB 15898, the expression and the secretion of neutral protease in concentrations exceeding 200 mg/l.

Figure 1:
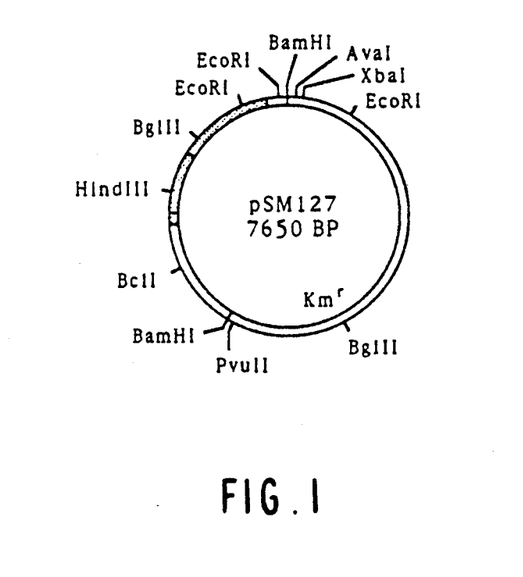
FIG. 1 shows the restriction map of the plasmid pSM127 formed by pUB110 and by the neutral protease gene.

The said hybrid plasmid, the map of which we set forth in FIG. 1, is formed by the neutral protease gene and by the plasmid pUB110, which assures the replication of pSM127 in *Bacillus subtilis* and contains the gene which codes for resistance to kanamycin.

Cells of *Bacillus subtilis* SMS108 containing the hybrid plasmid pSM127 have been deposited with the Northern Regional Research Center, Peoria, Ill. as NRLLB 15900. We have now, identified in the BclI-Hind III fragment of pSM127 of 811 base pairs (bp) a DNA region, defined by nprR2, responsible for the high production of neutral protease and located on the 5' terminal of the neutral protease gene.

In accordance with this, the object of the present invention consists in the use of the hybrid plasmid pSM127 as cloning vector of *Bacillus subtilis* for the expression of sequences of heterologous DNA and the production and secretion of proteins coded by the said sequences of heterologous DNA in high yields.

The object of the present invention further consists in molecules of recombinant DNA which are formed by the cloning vector pSM127, (which contains the replicon of pUB110 compatible with *Bacillus subtilis* and the gene which codes for resistance to kanamycin) and by the sequence of heterologous DNA which codes for the protein of interest and wherein the said sequence of heterologous DNA is inserted at a restriction site present on the neutral protease gene pSM127 and is under the control of the promoter regions, a site of recognition of the ribosomes, nprR2 and a signal sequence of the neutral protease. A further object of the present invention consists in *Bacillus subtilis* strains transformed with the said molecules of recombinant DNA and capable of expressing the sequences of heterologous DNA and producing and secreting the proteins coded by the said sequences. Moreover, the object of the present invention includes a process for the production of heterologous proteins which comprises the culturing, in a suitable culture medium, of a *Bacillus subtilis* strain transformed with the said molecules of recombinant DNA.

Definitions of the terms used in the present specification.

Expression—is the process by means of which a fragment of DNA or gene produces a protein. This takes place by a process of transcription, i.e. production of mRNA from the DNA fragment, and translation, i.e. production of the protein from mRNA.

Cloning vector of *Bacillus subtilis*—is a plasmid carrying a replicon which permits the vector to become replicated within host cells of *Bacillus subtilis* and one or more restriction sites at which the vector may be cut without impairing its essential biological functions.

Preferably, the said vector has a marker which is useful for the identification of transformant cells, such as, for example, kanamycin resistance or chloramphenicol resistance.

Molecule of recombinant DNA—is a DNA molecule formed by various gnomes which have been attached to each other outside the cell, and which has the capacity to be maintained within the host cells.

The presence, on the hybrid plasmid pSM127, of a region responsible for the overproduction of the neutral protease and its location within the BclI-Hind III fragment of 811 base pairs was verified by proceeding in the following manner.

The chloramphenicol acetyltransferase (CAT) gene which codes for the resistance to chloramphenicol, contained in the HpaII-MboI fragment of 1031 bp of the plasmid pC194 (BGSC 1E17), was isolated by treating the plasmid pC194 with the HpaII restriction enzyme and subsequently attaching the plasmid thus linearized to the fragment of 587 bp of the pE194 obtained following digestion of the plasmid pE194 (BGSC1E7) with the TaqI and MboI restriction enzymes.

The linear molecule of the pC194 may be attached to the TaqI-MboI fragment of the pE194 in a manner such as to form a linear molecule of 3497 bp, provided that the HpaII cohesive end of pC194 and the TaqI cohesive end of pE194 can be attached to each other.

The said molecule of 3497bp is thus treated with the MboI restriction enzyme, and there follows the isolation of an MboI-MboI linear fragment of DNA of 1618 bp, formed by the MboI fragment of 1031 bp of pC194 and by the TaqI-MboI fragment of 587 bp of pE194.

The linear fragment of 1618 bp obtained in this manner is then attached to the hybrid plasmid pSM127, after cutting of the pSM127 with the BclI restriction enzyme.

There is thus obtained the plasmid pSM153, formed by the DNA of the pSM127 and by that of the MboI-MboI fragment of 1618 bp. The plasmid pSM153 is then cut with the BamHI enzyme, which generates two fragments, one of approximately 5000 bp carrying the entire sequence of the pUB110, and the other, of approximately 4700 bp, having the gene which codes for the neutral protease and the CAT gene which codes for chloramphenicol resistance.

The fragment of 4700 bp is then used to transform cells of *Bacillus subtilis* BGSC 1A1, a low producer of neutral protease sensitive to chloramphenicol, selecting the transformed products obtained for resistance to chloramphenicol ($Cm^R$).

The transformation of *Bacillus subtilis* BGSC1A1 takes place only if there is an integration of the said fragment in the bacterial chromosome.

The integration may take place if on the BamHI fragment of pSM153 there is present the region homologous with the chromosomal DNA constituted by the neutral protease gene.

Figure 4:
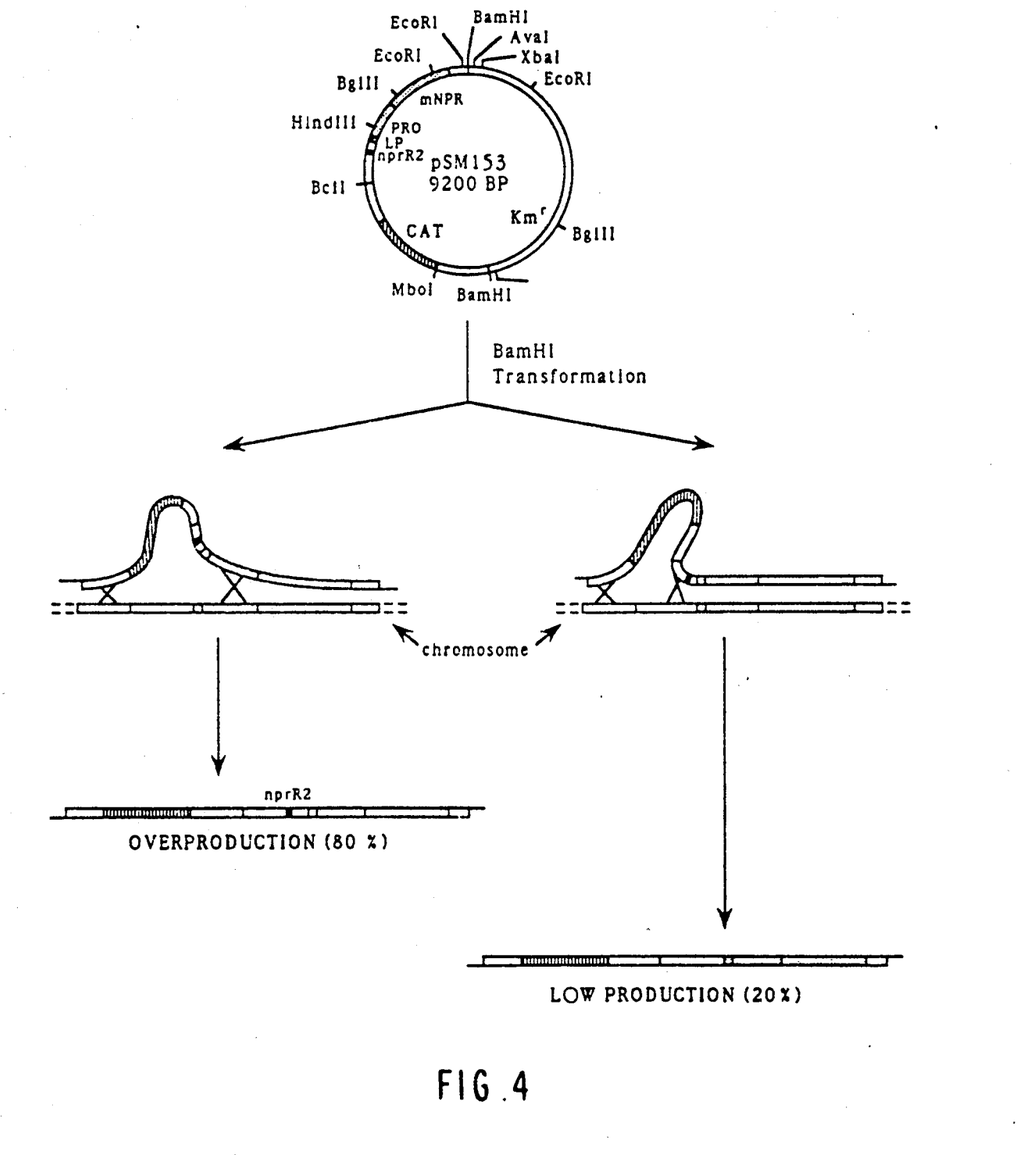
FIG. 4 shows the two possible recombinations between the bacterial chromosome of *Bacillus subtilis* BGSC 1A1 and the fragment of pSM153 of 4700 base pairs containing the CAT gene and the nprR2 region.

As shown in FIG. 4, a double crossing-over may take place between the chromosomal DNA and the plasmid DNA in the regions located below and above the CAT gene. This leads to an insertion of the CAT gene which codes for the resistance to Cm at the chromosomal level and, consequently, to the obtaining of Cm-resistant cells of *Bacillus subtilis* BGSC1A1 ($Cm^R$)

In addition to the integration of the CAT gene, the double crossing-over may lead to the integration of the nprR2 region, which regulates the overproduction of the neutral protease if the latter is however present on the plasmid pSM127.

For this reason, the *Bacillus subtilis* strain BGSC 1A1 is a low producer of neutral protease, and the integration at the chromosomal level of the nprR2 region ought to raise substantially the proteolytic activity of the said strain.

In fact, it was found that 80% of the said $Cm^R$*Bacillus subtilis* strains exhibited a proteolytic enzymatic activity 100 times greater than the parent strain BGSC 1A1, thus confirming the presence on the pSM127 of the nprR2 region and the correlation between the said region and the overproduction of neutral protease.

Figure 2A:
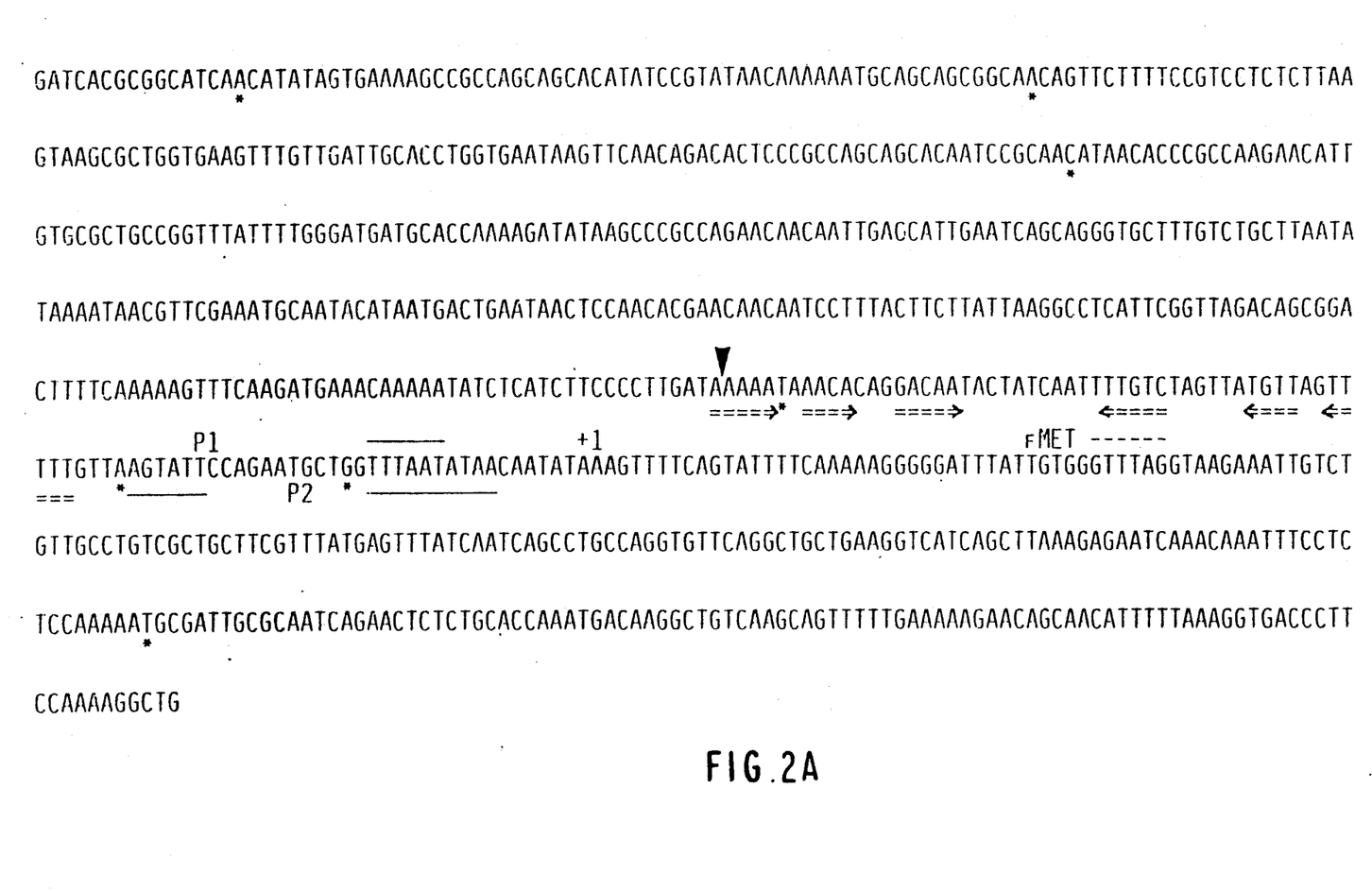
FIG. 2A and FIG. 2B show the nucleotide sequence of the nprR2 region responsible for the overproduction of the neutral protease (FIG. 2A) and of the same region present in front of the neutral protease gene in the *Bacillus subtilis* strain BGSC 1A1 (FIG. 2B).
Figure 2B:
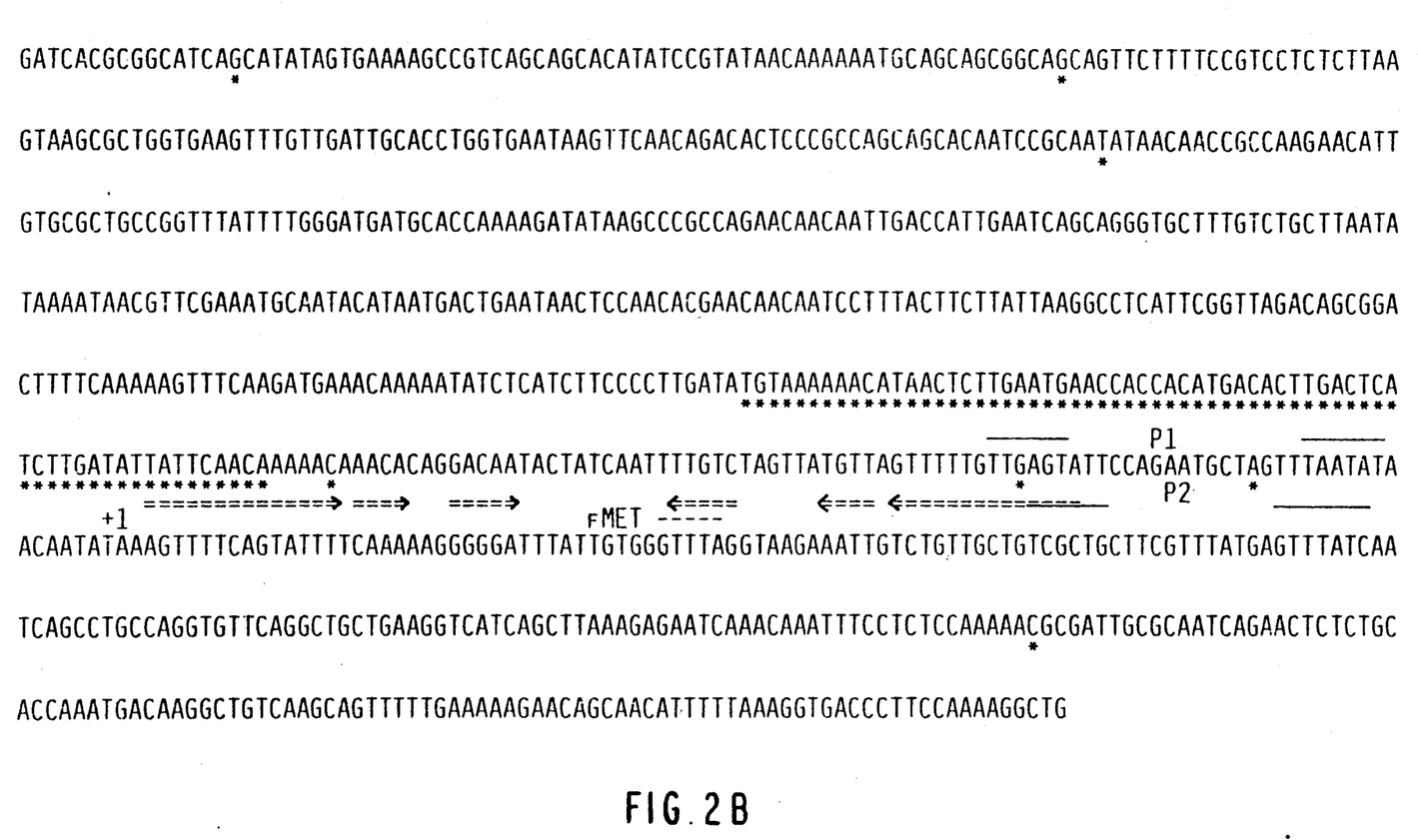

FIG. 2A sets out the sequence of DNA of the nprR2 region, and FIG. 2B that of the same region of DNA present in front of the neutral protease gene in the BGSC 1A1 *Bacillus subtilis* strain. As it is possible to observe, the nprR2 region is differentiated from that of *Bacillus subtilis* BGSC 1A1 in that there is a deletion of 66 base pairs at a distance of 124 bp from the origin of the gene.

In accordance with that according to the present invention, the hybrid plasmid pSM127 is used as a cloning vector for the expression of sequences of heterologous DNA and the production of proteins coded by the said sequences in *Bacillus subtilis* in high yields.

The hybrid plasmid pSM127 (FIG. 1) exhibits restriction sites within the neutral protease gene, at which sites it may be cut without impairing the nprR2 control sequences, the promoter, the recognition site of the ribosomes (RBS), and the signal sequence (PRE) which is responsible for the secretion of the neutral protease.

In particular, the restriction sites at which the cloning vector may be cut are HindIII, located in the PRO region, which is situated above the sequence which codes for the mature neutral protease, and the BglII and EcoRI sites present in the DNA region which codes for the mature neutral protease.

Figure 5:
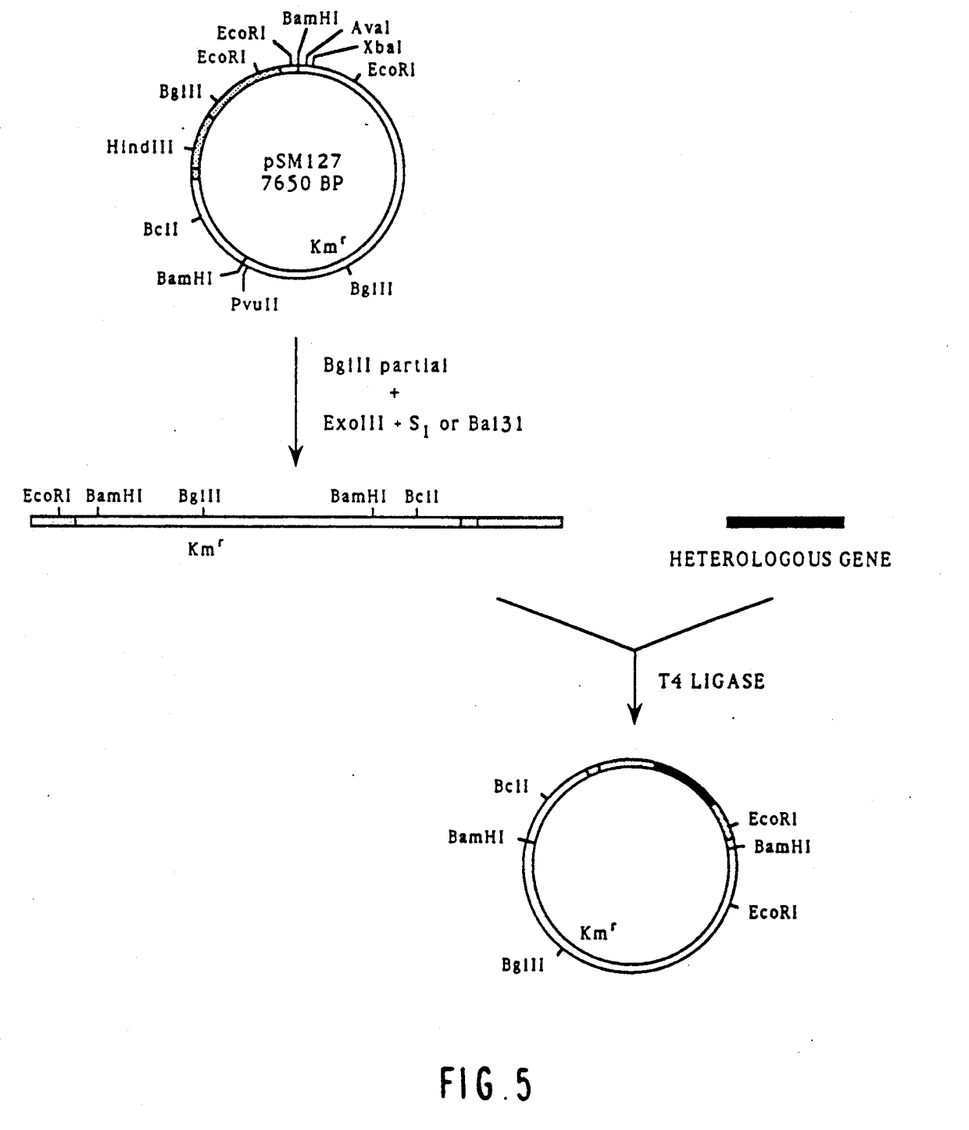
FIG. 5 shows the structure of a molecule of recombinant DNA in which the heterologous gene is inserted at the BglII restriction site of pSM127.
Figure 6:
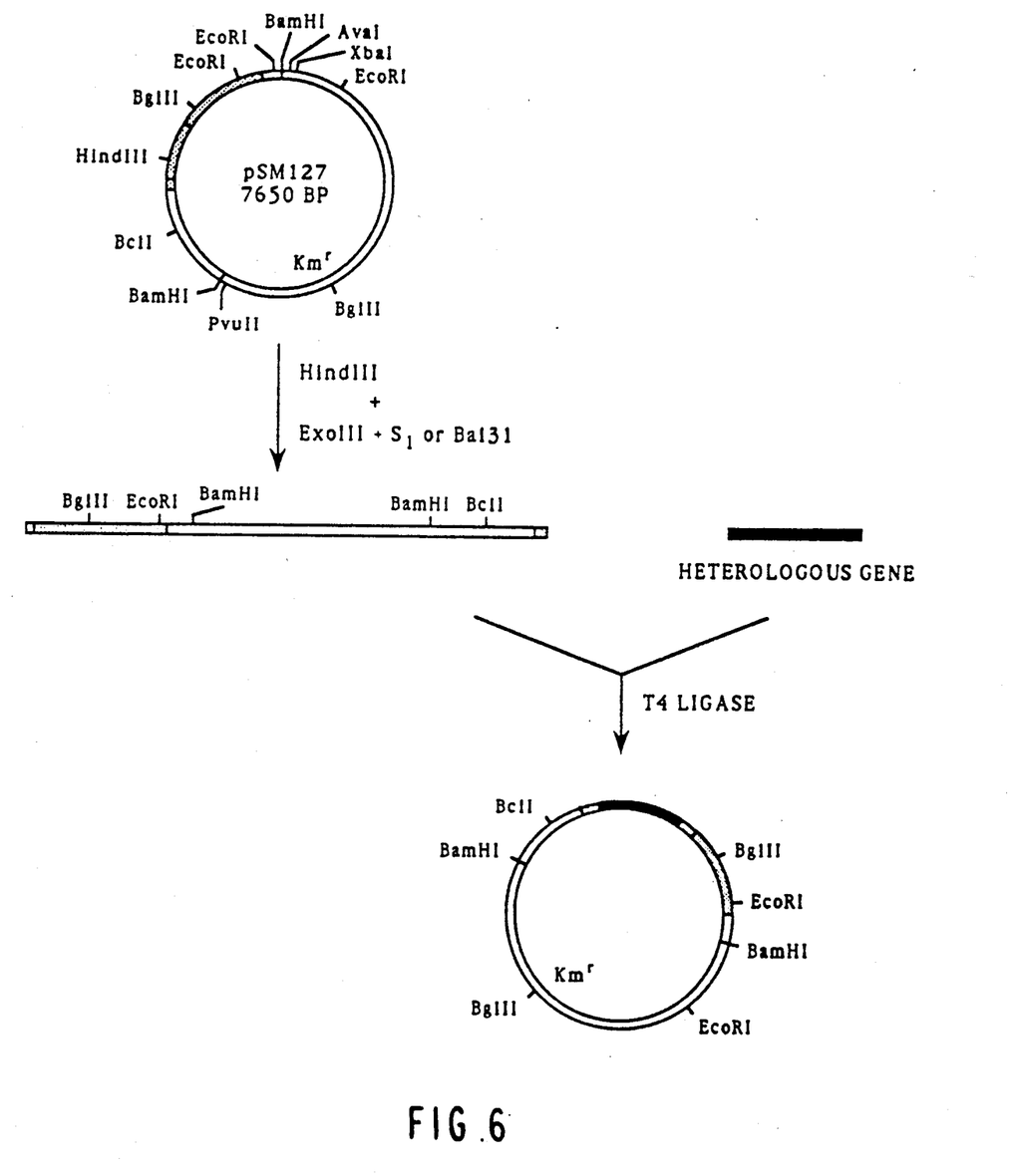
FIG. 6 shows the structure of a molecule of recombinant DNA in which the heterologous gene is inserted at the HindIII restriction site of pSM127.

The cloning vector cut in this manner is then attached to the expedient sequences of heterologous DNA in such a manner as to produce a fused gene, that is to say constituted by part of the neutral protease gene and by the sequence of heterologous DNA which is inserted in the cloning vector (FIG. 5 and FIG. 6).

The molecules of recombinant DNA which are obtained in this manner are formed by the cloning vector pSM127, which contains the replicon of pUB110 compatible with *Bacillus subtilis* and the gene which codes for the resistance to kanamycin, and by the fused gene, the expression of which is assured by the presence of the promoter and RBS sequences, and the overproduction and secretion of which are assured by the presence of the nprR2 and PRE regions respectively.

*Bacillus subtilis* strains transformed with the said recombinant molecules are capable of expressing the sequence of heterologous DNA and of producing and secreting the proteins coded by the said sequences in high yields.

The cloning vector, the molecules of recombinant DNA, *Bacillus subtilis* host cells and the methods of the present invention permit the expression of sequences of heterologous DNA and the production and secretion of the proteins coded by the said sequences.

Examples of such proteins include␣8-lactamase, the growth hormone and human calcitonin.

In accordance with the present invention, the plasmid pSM127 has been utilized for the cloning of the gene which codes for human calcitonin.

Human calcitonin is a hormone which controls the level of calcium in the blood.

This hormone is currently produced by chemical synthesis.

According to the present invention, a DNA fragment has been synthesized, having the following characteristics: it contains the nucleotide sequence which codes for the 32 amino acids constituting the human hormone, it possesses the end group which permits its insertion in the BglII restriction site present in the neutral protease gene on the plasmid pSM127, it exhibits a nonsense triplet after that coding for the terminal amino acid of calcitonin, the nucleotide sequence is such that, once the DNA fragment has been inserted at the BglII restriction site, the calcitonin sequence is arranged with the same direction of reading as the neutral protease.

This permits the obtaining of the synthesis of calcitonin, there being no stop codon in front of the start triplet of the calcitonin itself.

The synthetic DNA fragment has been cloned in the plasmid pSM131, the structure of which is set forth in Italian Patent Application 19960-A185, characterized by the presence of a single BglII restriction site, for the purpose of being able to preserve, to sequence and to amplify it.

The hybrid plasmid pSM170, constituted by the pSM131 and by the synthetic DNA fragment, was then purified, and the sequence of the cloned fragment was verified by means of the Maxam and Gilbert method (Methods in Enzymology (1980) Vol. 65, 499–560).

The synthetic DNA fragment, isolated from the plasmid pSM170, was subsequently attached to the cloning vector pSM127, after partial digestion of the said vector with the BglII restriction enzyme, in the presence of the enzyme $T_4$ ligase at a temperature of 14° C. and for a period of 16 hours. The ligase mixture obtained in this manner was used to transform cells of *Bacillus subtilis* SMS108 (NRLL15898) rendered competent in accordance with the Contente and Dubnau method (Mol. Gen. Genet. 167 (1979) 251–258).

The transformants were selected for kanamycin resistance ($Km^R$) and the absence of caseinolytic activity, spreading the cells on an NB culture medium.

The plasmids were extracted from the colonies of *Bacillus subtilis* SMS108(NRRLB 15898), $Km^R$ and having no ring, by the rapid extraction procedure, and were analyzed for the purpose of identifying those plasmids containing the synthetic DNA fragment.

The analysis was carried out by digesting the plasmids with the BglII restriction enzyme and separating the fragments obtained in the digestion reaction on a 7.5% acrylamide gel.

Figure 7:
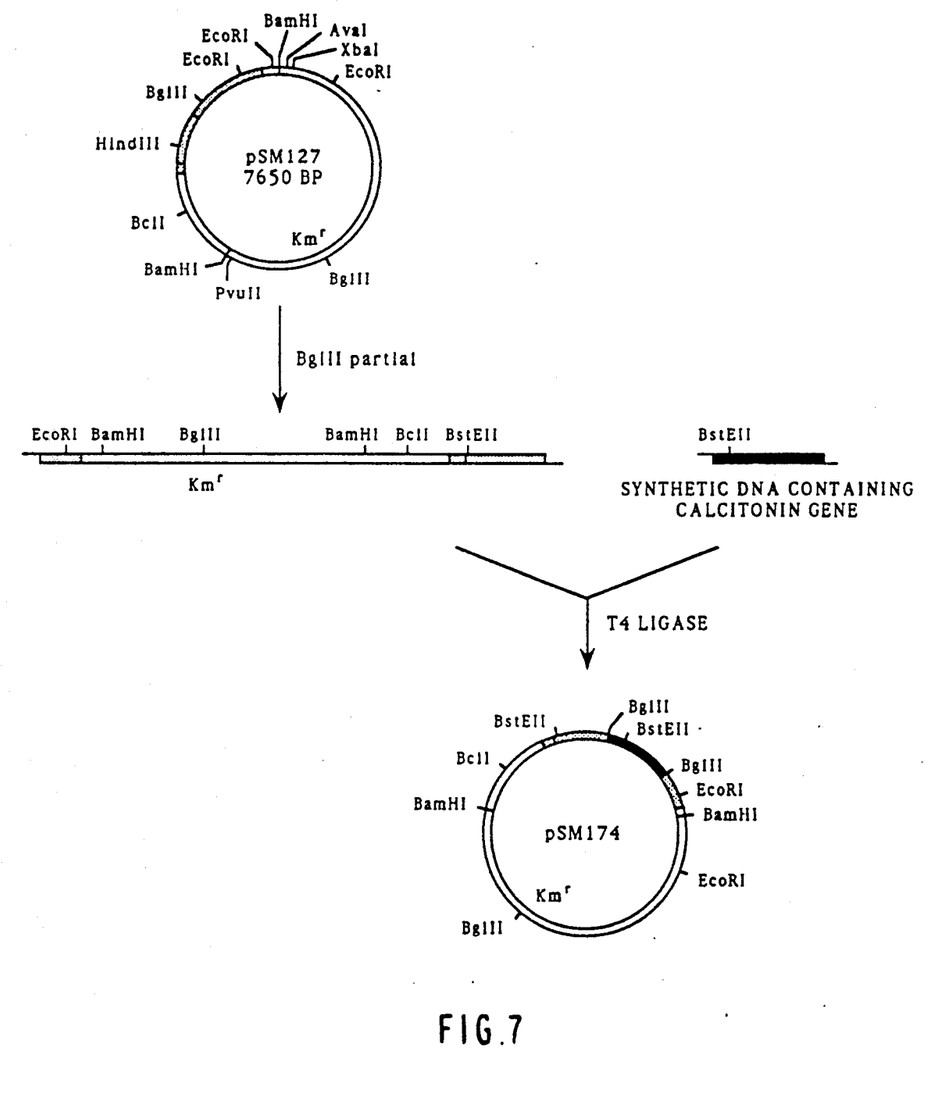
FIG. 7 shows the structure and the restriction map of pSM174, containing the synthetic DNA together with the calcitonin gene.

Among the plasmids which were examined, the plasmid pSM174 was identified, this being formed from the pSM127 and from the synthetic DNA fragment of calcitonin, oriented in such a manner as to have the correct reading of the sequence (FIG. 7).

The *Bacillus subtilis* strain SMS108 (pSM174) was deposited at the collection center "American Type Culture Center" on 26/6/1985.

The capacity of the *Bacillus subtilis* strain SMS108 (pSM174) to express and to secrete human calcitonin was verified by culturing the strain in a VY culture medium (DIFCO) at 37° C. and analyzing aliquot of the supernatant at various intervals of time, by means of radioimmunological analysis (RIA).

The experimental examples which follow are illustrative and non-limitative as regards the invention itself.

EXAMPLE 1

A. Isolation of a MboI fragment carrying the chloramphenicol acetyltransferase (CAT) gene of the pC194

5 µg of the plasmid pC194 (BGSC 1E17) are linearized in 50 µl reaction volume with 5 units (U) of HpaII restriction enzyme (Boehringer-Mannheim) under the conditions suggested by the supplier company.

The solution is then treated with an equal volume of phenol saturated with TE (10 mM Tris-HCl, 1mM EDTA), and the plasmid DNA is precipitated with 1/10 volume of 3M sodium acetate and 2.5 volumes of 95% ethanol.

The reaction mixture is centrifuged at 10,000 revolutions per minute for 10 minutes, the DNA is removed, dried under vacuum and then resuspended in 100 μl of solution containing 66 mM Tris-HCl (pH 7.5), 6 mM MgCl₂, 10 mM dithiothreitol, 1 mM adenosine triphosphate (ATP), 5 μg of the TaqI-MboI fragment of 587 base pairs (bp) of the plasmid pE194 (BGSC 1E7) and 10 U of T₄ DNA ligase.

The ligase reaction is carried out by maintaining the solution at a temperature of 14° C. for 18 hours.

The fragment of 587 bp of the pE194 (BGSC 1E7) was obtained by digesting 20 μg of the plasmid with 20U of the TaqI and MboI enzymes, operating in accordance with the specifications of the supplier company (Boehringer-Mannheim) and was subsequently purified by a 5% acrylamide gel as described in Maxam and Gilbert (Methods in Enzymology, vol. 65 (1980) 499-560).

The linear molecule of the pC194 is attached to the TaqI-MboI fragment of the pE194, thus forming a linear molecule of 3497 bp, in which the HpaII and TaqI cohesive ends can be attached to each other.

On conclusion of the ligase reaction, the mixture is treated with phenol, and the DNA is precipitated and removed as reported above.

The DNA is then resuspended in 50 μl of a solution containing 75 mM NaCl, 10mM Tris HCl (pH 7.4), 10 mM MgCl₂ and 1mM dithiothreitol, and is treated with 2U of MboI restriction enzyme for 1 hour at 37° C.

Figure 3:
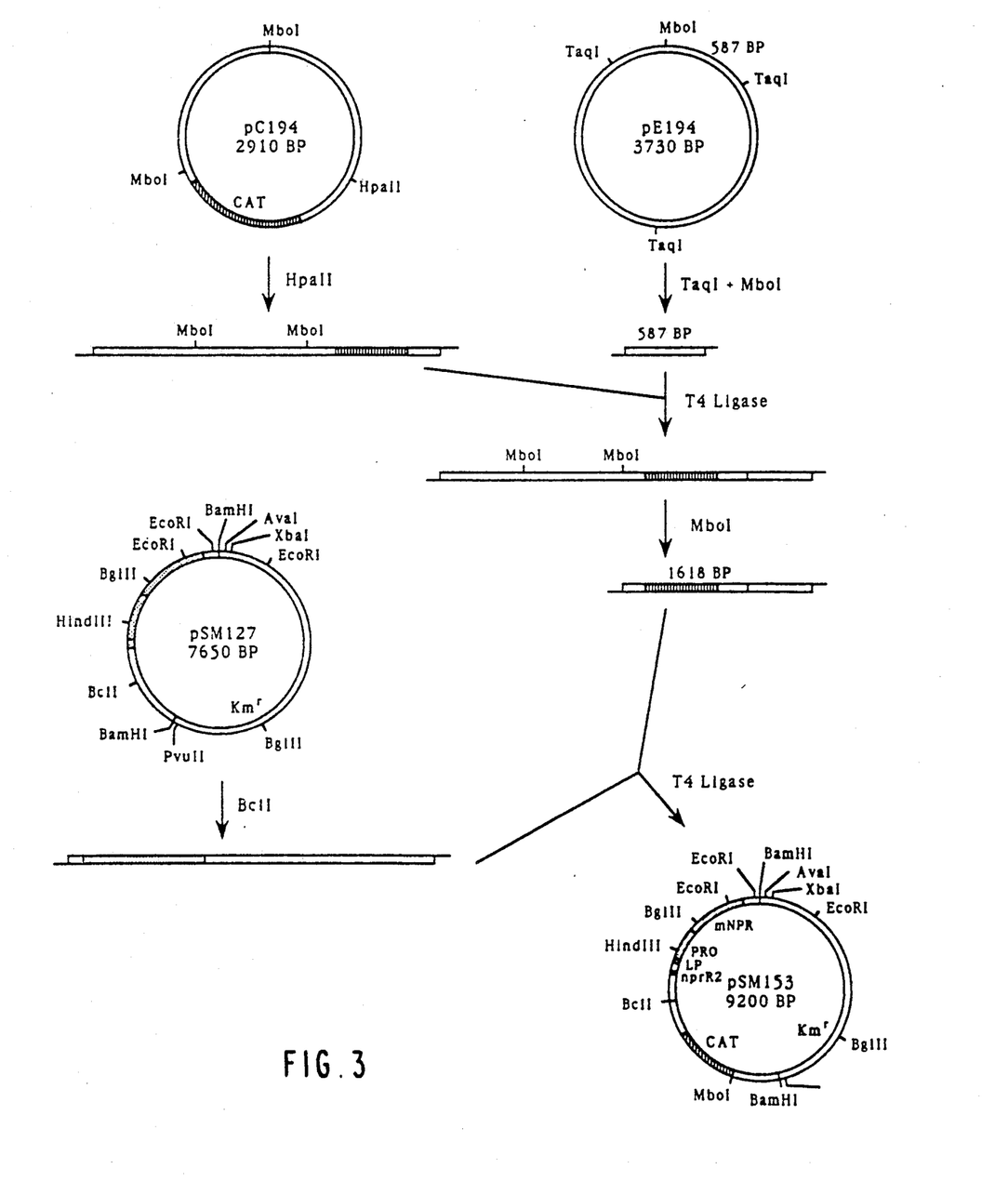
FIG. 3 shows the construction of the plasmid pSM153 formed by the CAT gene of pC194 and by the plasmid pSM127.

After this, the DNA is loaded onto a 5% acrylamide gel, and the linear fragment of 1618 bp is eluted, this being formed from the MboI-HpaII fragment of 1031 bp of the pC194 and from the TaqI-MboI fragment of 587 bp of the pE194 (FIG. 3).

B. Insertion of the linear DNA fragment of 1618 bp at the BclI site of the plasmid pSM127 and isolation of the plasmid pSM153

0.5 μg of the plasmid pSM127, digested with 1U of BclI restriction enzyme in accordance with the specifications of the supplier company (Boehringer-Mannheim), is suspended in 10 μl of a solution containing 66 mM Tris-HCl (pH 7.5), 6.6 mM MgCl₂, 10 mM dithiothreitol, 1 mM EDTA, 1 μg of the DNA fragment as obtained in A) and 1 U of T₄ DNA ligase.

The reaction is carried out at 14° C. for 18 hours and, after inactivation of the enzyme at 65° C. for 10 minutes, the mixture is used to transform cells of Bacillus subtilis SMS108 (NRLLB 15898), sensitive to chloramphenicol and kanamycin, rendered competent in accordance with the procedure described by Contente and Dubnau in (Mol. Gen. Genet. 167 (1978) 251-258).

The selection of the transformants is undertaken on NB plates, the composition of which is described in Example 2, containing 1% casein and 5 pg each of kanamycin and chloramphenicol.

The plasmid pSM153, whose map is set forth in FIG. 3, is isolated from one of the colonies which are kanamycin-resistant (Km^R) and chloramphenicol-resistant (Cm^R).

The plasmid pSM153 is formed from the DNA of the pSM127 and from the MboI-MboI fragment of 1618 bp containing the CAT gene.

The insertion of the MboI-MboI fragment in the orientation found in pSM153 permits the reconstruction of a BclI site from the proximal part to the neutral protease gene.

In fact, the four cohesive bases of the MboI site of pE194, GATC, are followed by an adenine (A), as a result of which, when the BclI cohesive ends of pSM127 and MboI are paired among themselves, there is originated the sequence TGATCA, which is recognized and cut by the BclI enzyme:

MboI-MboI fragment

This does not take place when there is union of the MboI site deriving from the pC194 with the BclI site of pSM127.

C. Verification of the presence of the nprR2 region on the pSM153

1 μg of the plasmid pSM153 is digested with 1U of the BamHI restriction enzyme in 10 pl of reaction volume in accordance with the specifications of the supplier company (Boehringer-Mannheim).

Cutting with BamHI produces two fragments, one of approximately 5,000 bp carrying the entire sequence of pUB110, and the other of approximately 4700 bp having the neutral protease gene and the fragment of 1618 bp coding for CAT.

The DNA digested in this manner is used to transform cells of Bacillus subtilis BGSC 1A1 which have been rendered competent as described by S. Contente and D. Dubnau, and selecting the transformants for resistance to chloramphenicol (3 μg/ml of NB medium).

The linear DNA molecules do not transform the Bacillus subtilis cells, unless they are integrated in the bacterial chromosome.

Accordingly, there are selected only the Cm^R colonies in which there has taken place the recombination of the BamHi fragment of 2350 bp which precedes the CAT gene and which contains the neutral protease gene and the fragment of approximately 750 bp which follows the CAT gene (FIG. 4) with the respective homologous regions of the bacterial chromosome.

Of the Cm^R colonies obtained in this manner, approximately 80% show a caseinolytic activity greater than that which can be found in the parent strain Bacillus subtilis BGSC 1A1.

The caseinolytic activity is demonstrated on NB plates containing casein, by examining the sizes of the rings. The increase in enzymatic activity confirms the presence of the nprR2 region on the DNA fragment present on the pSM153 and, consequently, on the pSM127.

EXAMPLE 2

Cloning of the human calcitonin gene, and preparation of pSM174

0.1 μg of the plasmid pSM131 is digested in 20 μl of a solution, 20 mM glycine - NaOH, 10 mM MgCl₂, 7 mM β-mercaptoethanol (pH 9.5), with 0.1 unit (U) of BglII enzyme (Boehringer-Mannheim) at a temperature of 37° C. for 1 hour.

After inactivation of the enzyme at 65° C. for 10 minutes, 2 μl of the digestion mixture (10 ng of the plasmid DNA) are added to 18 μl of a solution of 66 mM Tris-HCl (pH 7.6), 6.6 mM MgCl$_2$, 10 mM dithiothreitol and 1 mM ATP containing 10 ng of the synthetic fragment of calcitonin and 0.1U of the enzyme T$_4$ DNA ligase (Boehringer-Mannheim).

The ligase reaction is carried out at 14° C. for hours.

After inactivation of the enzyme at 65° C. for 10 minutes, 10 µl of the ligase mixture are used to transform cells of *E. coli* HB101 rendered competent in accordance with the method described by Mandel and Higa (J. Mol. Biol. 53 (1970) 159–162). The selection of the transformants is carried out on plates of L agar (DIFCO) containing 15 µg/ml of tetracycline (Tc).

From a Tc$^R$ colony there is purified the plasmid pSM170, which contains the synthetic calcitonin fragment.

The sequence of the cloned fragment is verified by applying the method of Maxam and Gilbert (Methods in Enzymology Vol 65 (1980), 499–560).

30 µg of the plasmid pSM170 are digested with 30U of the BglII enzyme, in 150 µl of solution containing 20 mM glycine-NaOH, 10 mM MgCl$_2$ and 7 mM β-mercaptoethanol (pH 9.5) at 37° C. for 1 hour. The plasmid DNA fragments obtained in this manner are separated on a 7.5% acrylamide gel, and the DNA fragment of 134 base pairs, containing the synthetic calcitonin fragment, is eluted in accordance with the method described by Maxam and Gilbert (Methods in Enzymology (1980) vol. 65, 526–527).

1 µg of pSM127 is digested with 1U of BglII enzyme in 50 µl of solution containing 20 mM glycine - NaOH, 10 mM MgCl$_2$, 7 mM β-mercaptoethanol (pH 9.5) at 37° C. for 1 hour.

After the addition of 120 ng of the DNA fragment of 134 bp to the digestion mixture, the DNA is precipitated at −80° C. for 20 minutes by adding 6 µl of 3M sodium acetate pH 5.5 and 150 µl of 98% ethanol. The precipitated DNA is separated from the reaction mixture by centrifuging at 10,000 revolutions per minute for 10 minutes, dried and resuspended in 10 µl of a solution of 66 mM Tris-HCl (pH 7.6), 46.6 mM MgCl$_2$, 10 mM dithiothreitol and 1 mM ATP containing 1U of T$_4$ DNA ligase.

After incubation of the said mixture at 14° C. for 16 hours and inactivation of the enzyme at 65° C. for 10 minutes, 5 µl of the ligase mixture are used to transform cells of *Bacillus subtilis* SMS108 (NRRLB 15898) rendered competent in accordance with the method of Contente and Dubnau (Mol. Gen. Genet. 167 (1979) 251–258).

The transformed cells are then selected for kanamycin resistance and the absence of caseinolytic activity on plates of NB medium with the following composition:

| | |
|---|---|
| DIFCO Nutrient Broth | 8.00 g |
| MgSO$_4$.7 H$_2$O | 0.25 g |
| KCl | 1.00 g |
| DIFCO Agar | 15.00 g |
| FeSO$_4$.7 H$_2$O | 0.28 g |
| MnCl$_2$ | 1.25 mg |
| Ca(NO$_3$)$_2$ | 164.00 mg |
| casein | 10.00 g |
| kanamycin | 5 mg |
| H$_2$O | 1 liter |

The plasmids are extracted from the Km$^R$ colonies having no ring, in accordance with the method described by Rodriguez and Tait (Recombinant DNA Techniques: an introduction (1983) Addison-Wesley Publishing Company). The plasmids containing the synthetic fragment are then identified by means of digestion with the BglII enzyme and separation of the plasmid DNA fragments obtained in this manner on a 7.5% acrylamide gel.

The orientation of the synthetic calcitonin fragment in pSM127 is verified by digesting the plasmids with the BstEII enzyme, the restriction site of which is located within the synthetic fragment and the neutral protease gene.

A correct orientation should produce two fragments, of approximately 7900 bp and 560 bp respectively, while the other orientation should produce one fragment of approximately 7900 bp and one of 650 bp.

The digestion of the plasmids obtained by rapid extraction was carried out with 1U of BstEII enzyme in 30 82 l of reaction volume and under the conditions specified by the supplier company (Boehringer-Mannheim). The plasmid DNA fragments are separated on 7.5% acrylamide gel.

It was thus possible to isolate the plasmid pSM174 (FIG. 7) which exhibits the synthetic calcitonin fragment inserted in pSM127 with a correct orientation.

The sequence analysis using the method of Maxam and Gilbert confirms the correctness of the structure obtained.

The capacity of the *Bacillus subtilis* SMS108 (pSM174) to express and to secrete human calcitonin was verified by radioimmunological analysis (RIA) of the supernatant.

Strains of *Bacillus subtilis* SMS108 (pSM174) and *Bacillus subtilis* SMS108 (NRRLB 15898) were cultured in 250 ml Erlenmeyer flasks, each containing 50 ml of VY (DIFCO veal infusion broth 25 g/l, yeast extract 5 g/l, H$_2$O liter) at a temperature of 37° C.

At intervals of 1 hour, 1 ml aliquots were taken from the culture broth and centrifuged for 10 minutes in an Eppendorff centrifuge, model 5414, at 4° C.

To the supernatants obtained in this manner were added the protease inhibitors phenylmethylsulphonyl fluoride (PMSF) and ethylenediaminotetraacetic acid (EDTA) at a final concentration of 1 mM and 5 mM respectively.

Aliquots of the supernatants treated in this manner were used for the RIA examination of the calcitonin, using the kit and the operating procedures of the supplier company Eiken Chemical Company, Ltd.

The results obtained are shown in Table 1.

TABLE 1

Radioimmunological analysis carried out with antibodies against human calcitonin, on culture supernatants taken at various times from the *Bacillus subtilis* strains SMS108 (pSM174) and SMS108.

| Time (hours) | SMS108 (pSM174) ng/ml | SMS108 ng/ml |
|---|---|---|
| 2 | 5.0 | 0.1 |
| 3 | 7.2 | " |
| 4 | 120.0 | " |
| 6 | 2200.0 | " |
| 8 | 4250.0 | " |
| 24 | 140.0 | " |

We claim:

1. A recombinant DNA molecule useful for expressing and secreting a heterologous protein in *Bacillus subtilis* comprising:

(a) a DNA sequence comprising an nprR2 regulating region, a promoter, a ribosome binding site and a signal secretion sequence of a neutral protease gene isolated from plasmid pSM127, said region having the nucleotide sequence given in FIG. 2a; and (b) a heterologous gene encoding said heterologous protein, wherein the expression of said heterologous gene is under the control of said DNA sequence.

2. The recombinant DNA molecule according to claim 1, wherein said heterologous gene codes for human calcitonin.

3. The recombinant DNA molecule according to claim 2, wherein the heterologous gene is inserted at the restriction site BglII.

4. The recombinant DNA molecule according to claim 3, present in *Bacillus subtilis* SMS108 (pSM174) having ATCC Deposit No. 53168.

5. The recombinant DNA molecule according to claim 1, obtained by a process comprising:

a') linearizing a plasmid pSM 127 present in *Bacillus subtilis* having NRRL deposit number NRRL-B-15900 by digestion with a restriction enzyme selected from the group consisting of HindIII, BglII and EcoRI, and b') binding in the presence of T4 DNA ligase the linearized plasmid obtained according to a') with said heterologous gene, where said heterologous gene has sticky ends with those of the linearized plasmid obtained according to a').

6. The recombinant DNA molecule according to claim 5, wherein in step a') the plasmid pSM 127 is digested with the restriction enzyme BglII in step b') the heterologous gene codes for human calcitonin.

7. A *Bacillus subtilis* microorganism transformed with the recombinant DNA molecule according to any of claims 1-4.

8. A microorganism according to claim 7, which is *Bacillus subtilis* SMS108 having NRRL deposit number NRRL-B 15898.

9. A process for expressing and secreting a heterologous protein comprising:

a'') cultivating in an appropriate culture medium, at a temperature of from 10° to 51° C. a transformed *Bacillus subtilis* microorganism according to claim 7, and b'') isolating from the culture medium and purifying the heterologous protein.

10. The process according to claim 9, wherein in step a'') the microorganism is *Bacillus subtilis* SMS 108 (pSM174) having ATCC Deposit No. 53168.

11. A process according to claim 9, wherein said heterologous protein is human calcitonin.

* * * * *